(12) United States Patent
Tearney et al.

(10) Patent No.: US 11,553,841 B2
(45) Date of Patent: Jan. 17, 2023

(54) SYSTEMS, DEVICES, METHODS, APPARATUS AND COMPUTER-ACCESSIBLE MEDIA FOR PROVIDING OPTICAL IMAGING OF STRUCTURES AND COMPOSITIONS

(71) Applicants: THE GENERAL HOSPITAL CORPORATION, Boston, MA (US); Trustees of Boston University, Boston, MA (US)

(72) Inventors: Guillermo J. Tearney, Cambridge, MA (US); Brett Eugene Bouma, Quincy, MA (US); Hongki Yoo, Melrose, MA (US); Milen Shishkov, Watertown, MA (US); Joseph Gardecki, Acton, MA (US); Roman Shubochkin, Arlington, MA (US); Theodore Morse, Little Compton, RI (US); Farouc Amin Jaffer, Jamaica Plain, MA (US)

(73) Assignee: The General Hospital Corporation, Boston, MA (US)

( * ) Notice: Subject to any disclaimer, the term of this patent is extended or adjusted under 35 U.S.C. 154(b) by 163 days.

(21) Appl. No.: 17/191,343

(22) Filed: Mar. 3, 2021

(65) Prior Publication Data

US 2021/0267460 A1 Sep. 2, 2021

Related U.S. Application Data

(60) Continuation of application No. 15/359,279, filed on Nov. 22, 2016, now Pat. No. 10,939,825, which is a
(Continued)

(51) Int. Cl.
*A61B 5/00* (2006.01)
*G01N 21/65* (2006.01)
(Continued)

(52) U.S. Cl.
CPC .......... *A61B 5/0084* (2013.01); *A61B 5/0066* (2013.01); *A61B 5/0071* (2013.01);
(Continued)

(58) Field of Classification Search
CPC ... A61B 5/0066; A61B 5/0071; A61B 5/0084; A61B 5/6852; G01B 9/02091; G01N 21/6456; G01N 21/65; G01N 2201/0866
See application file for complete search history.

(56) References Cited

PUBLICATIONS

Ryu, S. Y., et al. "Combined system of optical coherence tomography and fluorescence spectroscopy based on double-cladding fiber." Optics letters 33.20 (2008): 2347-2349.
(Continued)

*Primary Examiner* — Mark D Remaly
(74) *Attorney, Agent, or Firm* — Quarles & Brady LLP

(57) ABSTRACT

Exemplary systems, devices, methods, apparatus and computer-accessible media for providing and/or utilizing optical frequency domain imaging (OFDI) and fluorescence of structures and, e.g., multimodality imaging using OFDI techniques and fluorescence imaging techniques are described. For example, an arrangement can provide at least one electro-magnetic radiation to an anatomical structure. Such exemplary arrangement can include at least one optical core and at least one cladding at least partially surrounding the fiber(s). A region between the optical core(s) and the cladding(s) can have an index that is different from indexes of the optical core(s) and the cladding(s). The arrangement can also include at least one apparatus which is configured to transmit the radiation(s) via the optical core(s) and the cladding(s) to the anatomical structure.

30 Claims, 11 Drawing Sheets

Related U.S. Application Data division of application No. 13/114,845, filed on May 24, 2011, now Pat. No. 9,557,154.

(60) Provisional application No. 61/353,424, filed on Jun. 10, 2010, provisional application No. 61/348,071, filed on May 25, 2010.

(51) Int. Cl.
  *G01B 9/02015* (2022.01)
  *G01B 9/02091* (2022.01)
  *G01B 9/02* (2022.01)
  *G01N 21/64* (2006.01)
  *G01N 21/47* (2006.01)

(52) U.S. Cl.
  CPC .......... *A61B 5/6852* (2013.01); *G01B 9/0205* (2013.01); *G01B 9/02029* (2013.01); *G01B 9/02091* (2013.01); *G01N 21/6456* (2013.01); *G01N 21/65* (2013.01); *G01N 21/4795* (2013.01); *G01N 21/64* (2013.01); *G01N 2201/0866* (2013.01)

(56) References Cited

PUBLICATIONS

European Patent Office. Communication pursuant to Article 94(3) EPC for application EP11787272.1. dated Nov. 17, 2020. 8 pages.

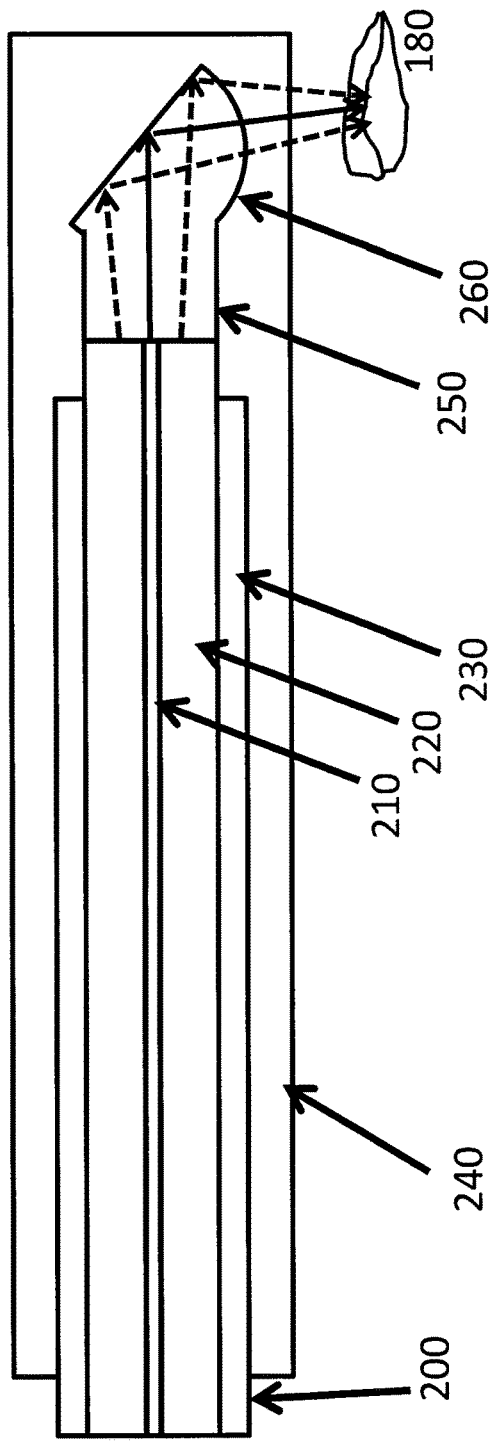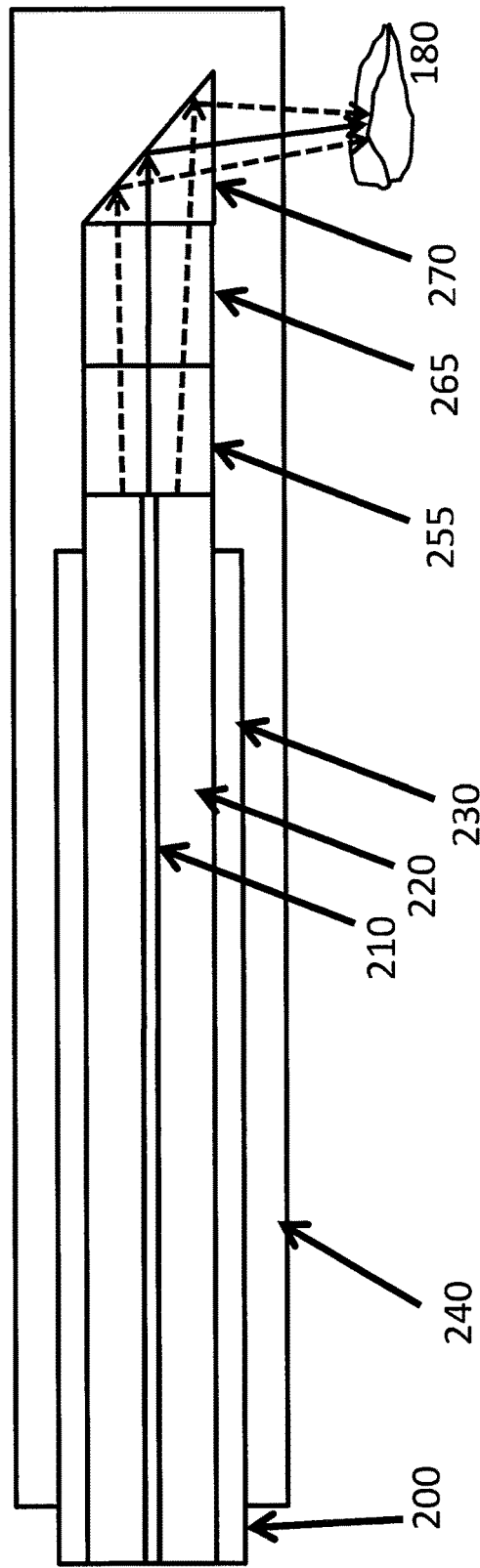

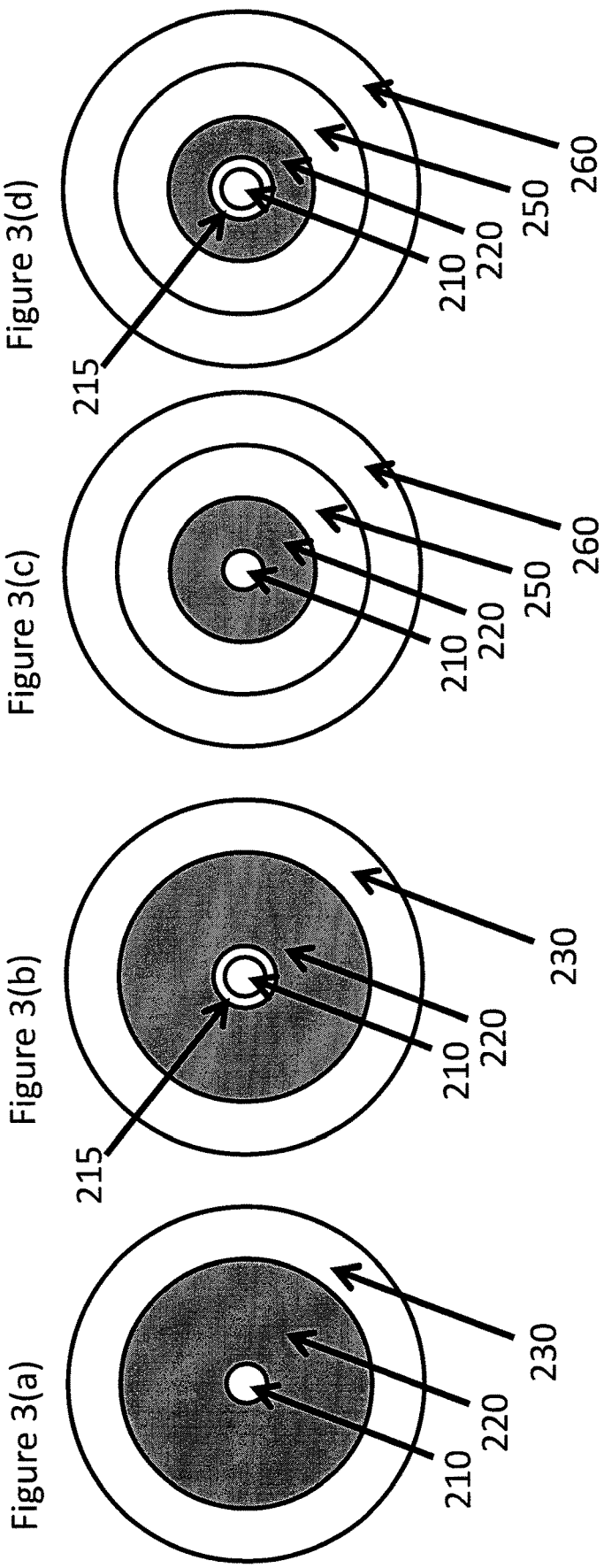

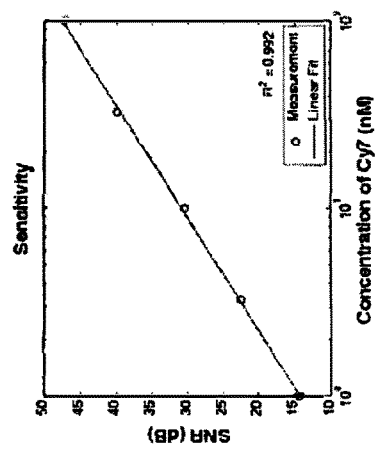
FIG. 7a
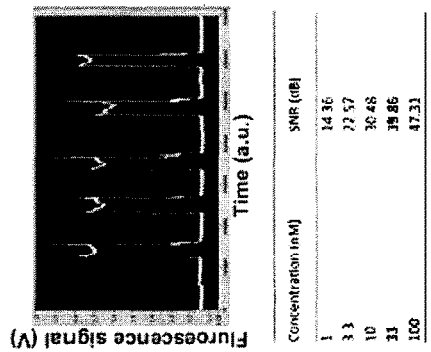
FIG. 7b
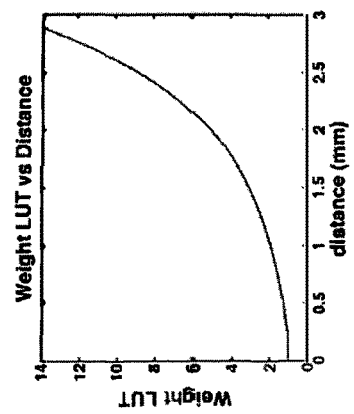
FIG. 7c
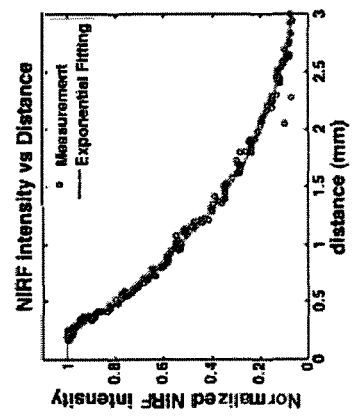
FIG. 7d
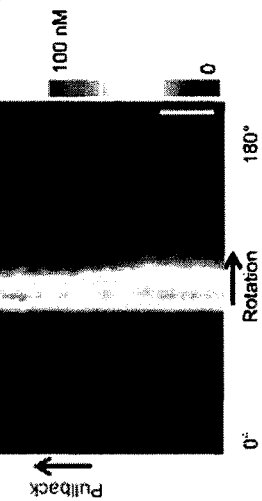
FIG. 7e
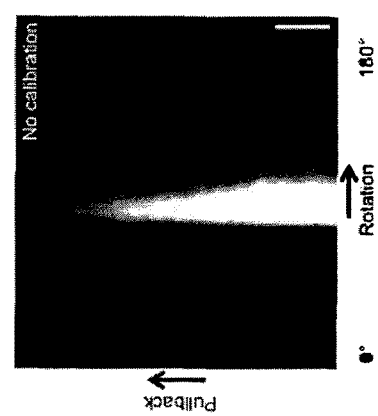
FIG. 7f
FIG. 7g

SYSTEMS, DEVICES, METHODS, APPARATUS AND COMPUTER-ACCESSIBLE MEDIA FOR PROVIDING OPTICAL IMAGING OF STRUCTURES AND COMPOSITIONS

CROSS-REFERENCE TO RELATED APPLICATIONS

This present application is a continuation of U.S. application Ser. No. 15/359,279 filed on Nov. 22, 2016, which is a divisional of U.S. application Ser. No. 13/114,845 filed on May 24, 2011, which is based on and claims priority from U.S. Patent Application Ser. No. 61/348,071, filed on May 25, 2010, and U.S. Patent Application Ser. No. 61/353,424, filed on Jun. 10, 2010, the entire disclosures of which are incorporated herein by reference.

FIELD OF THE DISCLOSURE

The present disclosure relates generally to exemplary systems, devices, methods, apparatus and computer-accessible media for providing optical imaging catheter of structures and compositions, and more particularly to systems, devices, methods, apparatus and computer-accessible media for providing and/or utilizing optical frequency domain imaging (OFDI) and fluorescence of structures and compositions and, e.g., multimodality imaging using OFDI techniques and fluorescence imaging techniques.

BACKGROUND INFORMATION

A majority of diseases arise within luminal organs such as the gastrointestinal tract and coronary arteries. Understanding and diagnosis of these diseases can require knowledge of their gross and microscopic structure, as well as their composition and molecular and cellular expression.

An optical imaging catheter has become an important tool to assess and diagnose diseases arising from luminal organs. This is the case, since many of the mechanisms involving diseases occur on a microscopic scale, high-resolution imaging techniques can be very important. Thus, optical imaging techniques, which are also considered to be relatively safe and non-toxic, are can be used for in vivo imaging. Optical frequency domain imaging (OFDI) or optical coherence tomography (OCT) imaging using rotationally scanning catheters can be used for studying cross-sectional and three-dimensional microstructure of luminal tissues. However, information such as molecular expression and tissue composition may not be ascertained from the OFDI signal. Other independently developed catheter-based imaging modalities, such as Raman spectroscopy, fluorescence imaging, near-infrared fluorescence (NIRF), time-resolved lifetime spectroscopy (TRLIFS), and near-infrared spectroscopy (NIRS) can provide this additional information. However, these exemplary techniques operate without knowledge of the underlying microscopic structure, making it difficult to place the acquired signatures in the appropriate morphologic context.

In order to resolve such possible issues and advance catheter-based diagnosis, it is therefore possible to obtain OFDI images in combination with data from these complementary modalities. Multimodality imaging techniques have been developed for cellular imaging under a microscope or small animal imaging due to relatively easy accessibility. However, in vivo multimodality imaging of luminal organs, such as coronary arteries, gastrointestinal tract, and respiratory system has not been appropriately described. Although multimodality imaging techniques in a catheter form have been utilized, such techniques could not provide comprehensive three-dimensional (3D) information from the luminal organs yet, due to the lack of fast rotation, high speed acquisition, and/or small catheter for in vivo data collection.

A sequential acquisition of such diverse information using multiple independent catheters and systems has, however, likely been untenable due to the impracticality of conducting multiple procedures, subject motion, and difficulties registering datasets. Thus, there may be a need to provide combined multimodality OFDI catheters and systems which can facilitate, e.g., a simultaneous acquisition of co-registered OFDI and complementary structural, compositional, and/or molecular data. In addition, it may be beneficial to address and/or overcome at least some of the deficiencies of the prior approaches, procedures and/or systems that have been described herein above.

SUMMARY OF EXEMPLARY EMBODIMENTS

It is therefore one of the objects of the present invention to reduce or address the deficiencies and/or limitations of such prior art approaches, procedures and systems. In accordance with certain exemplary embodiments of the present disclosure, exemplary systems, devices, methods, apparatus and computer-accessible media can be provided which facilitate a simultaneous multimodality imaging of biological tissues, such as, e.g., luminal organs in vivo, using optical techniques.

According to one exemplary embodiment of the present disclosure, a device/apparatus can be provided which can include a multimodality catheter that illuminates the tissues and collects signals from the inside of the lumen, a multimodality system which generates light sources, detects returning lights, and processes signals, and a multimodality rotary junction which rotates and pulls back the catheter and connects the moving catheter to the stationary system. In another exemplary embodiment, a dual-modality catheter system can be provided for simultaneous microstructural and molecular imaging of arteries in vivo.

For example, according to one exemplary embodiment of the present disclosure, an arrangement can provide at least one electro-magnetic radiation to an anatomical structure. Such exemplary arrangement can include at least one optical core and at least one cladding at least partially surrounding the fiber(s). A region between the optical core(s) and the cladding(s) can have an index that is different from indexes of the optical core(s) and the cladding(s). The arrangement can also include at least one apparatus which is configured to transmit the radiation(s) via the optical core(s) and the cladding(s) to the anatomical structure.

The exemplary apparatus can be provided in an optical coherence tomography system. Further, a system can be provided which obtains information regarding the anatomical structure and/or molecular/chemical/biological compositions based on the radiation(s) using a fluorescence modality (e.g., exogenous and/or endogenous). In addition or alternatively, the system can obtain information regarding the anatomical structure and/or molecular/chemical/biological compositions based on the radiation(s) using optical frequency domain interferometry (OFDI) modality, spectral domain optical coherence tomography (SD-OCT) modality, time domain optical coherence tomography (TD-OCT) modality, near-infrared modality, Raman modality, photo acoustics modality, confocal modality, ablation modality, and/or lifetime modality. The near-infrared modality can be a near infrared spectroscopy modality.

The exemplary apparatus can also be provided in a probe, a catheter, an eye box, an endoscope, etc. Further, at least one additional cladding can at least partially surround the cladding(s). In addition, at least one further cladding can at least partially surround the additional cladding(s).

According to yet another exemplary embodiment of the present disclosure, method and computer-accessible medium can be provided for determining at least one characteristic of at least one structure or composition. Using such method and/or computer-accessible medium, it is possible to receive first data associated with the structure(s), where the first data include information which facilitates a correction of a physical parameter associated with the structure(s). Second data associated with the at least one structure or composition can be received which is different from the first data. The first and second data can be obtained from substantially the same location on or in the structure(s). Further information associated with the second data can be ascertained based on the physical parameter. Then, the characteristic(s) of at least one structure or composition can be determined based on the further data.

For example, the first data can include optical coherence tomography data. The second data can include optical florescence data. The physical parameter can be a distance from a catheter to an artery wall, a tissue, lumen, etc. of the structure(s). The further information can include a concentration of a molecule, cell, or a chemical, either resident in tissue or injected or administered subcutaneously or orally. The computer-accessible medium can include instructions. When the instructions are executed by a computer arrangement, the computer arrangement is configured to perform the above described exemplary procedures.

According to yet further exemplary embodiment of the present disclosure, an arrangement can be provided for transmitting at least one electro-magnetic radiation between at least two separate waveguides in an optical fiber. Such exemplary arrangement can include at least one first waveguide, such as, e.g., a core, and at least one second waveguide, such as, e.g., a cladding, where the optical fiber, which contains the first waveguide(s) and/or the second waveguide(s), can be rotatable. At least one first optical arrangement can be provided which communicates with the first waveguide and/or the second waveguide to transmit the at least one electro-magnetic radiation therethrough. At least one second arrangement can be provided which is configured to rotate the first optical fiber which contains the first waveguide and/or the second waveguide. In addition, at least one third arrangement can be provided which is configured to separate at least one portion of the electro-magnetic radiation(s) into at least one first radiation and at least one second radiation having different wavelengths.

For example, such third arrangement(s) can include a beam splitter, a pinhole mirror, and/or a dichroic mirror arrangement. The first radiation and/or the second radiation can, e.g., (i) have a wavelength that changes over time, or (ii) be a fluorescence radiation. The first radiation and/or the second can be is a pulsed radiation and/or a continuous radiation. At least one fourth arrangement can also be provided which is configured to generate at least one image of a sample as a function of the first optical coherence tomography radiation and the second florescence radiation. The generated image(s) can be provided for an anatomical structure (e.g., a lumen). The third arrangement(s) can include a double clad fiber coupler.

These and other objects, features and advantages of the exemplary embodiment of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying figures showing illustrative embodiments of the present disclosure, in which:

FIG. 2(a) is a side cross-sectional view of a multimodality optical imaging catheter with a side-viewing ball lens according to one exemplary embodiment of the present disclosure;

FIG. 2(b) is a side cross-sectional view of the multimodality optical imaging catheter with a GRIN lens and a prism according to another exemplary embodiment of the present disclosure;

FIG. 3(a) is a front cross-sectional view of a double-clad fiber with ultra low index coating according to an exemplary embodiment of the present disclosure;

FIG. 3(b) is a front cross-sectional view of a cross-talk suppressed double-clad fiber with an ultra-low index coating according to another exemplary embodiment of the present disclosure;

FIG. 3(c) is a front cross-sectional view of the double-clad fiber with two claddings according to yet another exemplary embodiment of the present disclosure;

FIG. 3(d) is a front cross-sectional view of the cross-talk suppressed double-clad fiber with two claddings according to still another exemplary embodiment of the present disclosure;

FIGS. 7(a)-7(g) are illustrations of experiment results on titration and distance calibration of fluorescence concentration by utilizing the exemplary systems, devices, methods, apparatus and computer-accessible media according to the present disclosure.

Figure 1A:
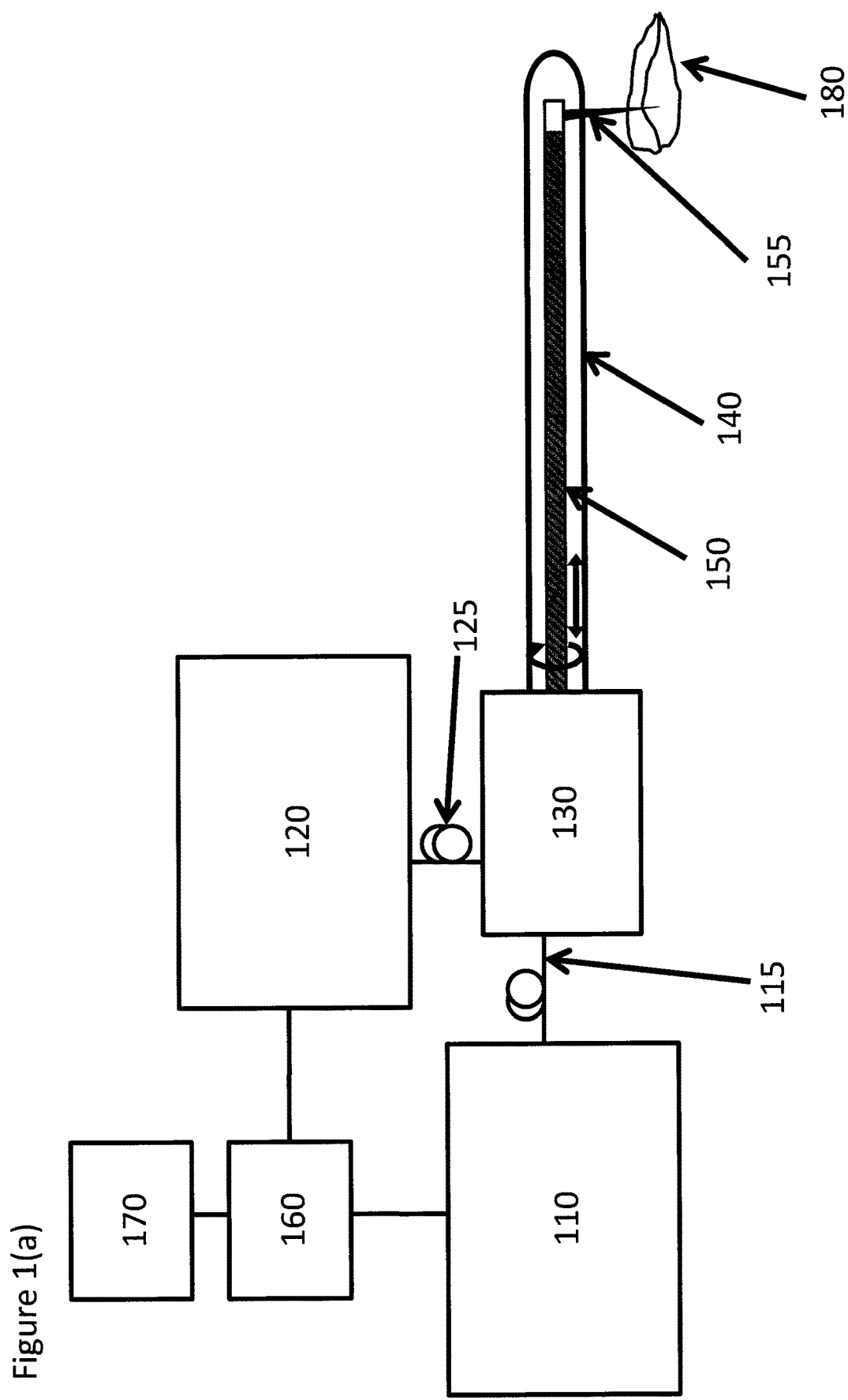
FIG. 1(a) is a schematic block diagram of an exemplary embodiment of a multi modality optical imaging catheter system and/or arrangement according to the present disclosure.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative embodiments. It is intended that changes and modifications can be made to the described exemplary embodiments without departing from the true scope and spirit of the subject disclosure as defined by the appended claims.

DETAILED DESCRIPTION OF EXEMPLARY EMBODIMENTS

A schematic block diagram of an exemplary embodiment of multi modality optical imaging catheter system according to the present disclosure is shown in FIG. 1(a). This exemplary apparatus of FIG. 1(a) can include a microstructural imaging system 110 (which can generate images using one or more processors), a single mode optical fiber 115, a molecular imaging system 120, a multimode optical fiber 125, a dual-modality rotary junction 130, a transparent imaging sheath 140, a dual-modality optical imaging catheter 150, a data acquisition system 160 and a data processing and storage unit 170. It should be understood that a plurality of each of these described systems, arrangements and elements can be included and/or implemented in or together with the exemplary apparatus of FIG. 1(a).

The microstructural imaging system 110 (e.g., one or more systems implementing one or more of optical frequency domain imaging, optical coherence tomography, etc. modalities) can detect a back-reflected light from a tissue 180 to acquire information and signals regarding tissue microstructures. The molecular imaging system 120 (e.g., one or more systems implementing one or more of near infra-red fluorescence imaging, fluorescence spectroscopy, Raman spectroscopy, fluorescence lifetime imaging, etc. modalities) can detect specific molecular information from the tissue 180, e.g., possibly but not necessarily using contrast agents. While the microstructural imaging system 110 can be connected to the dual-modality rotary junction 130 by the single mode fiber 115, the multi mode fiber 125 can be used for, e.g., the molecular imaging modality to achieve a high light efficiency.

Figure 1B:
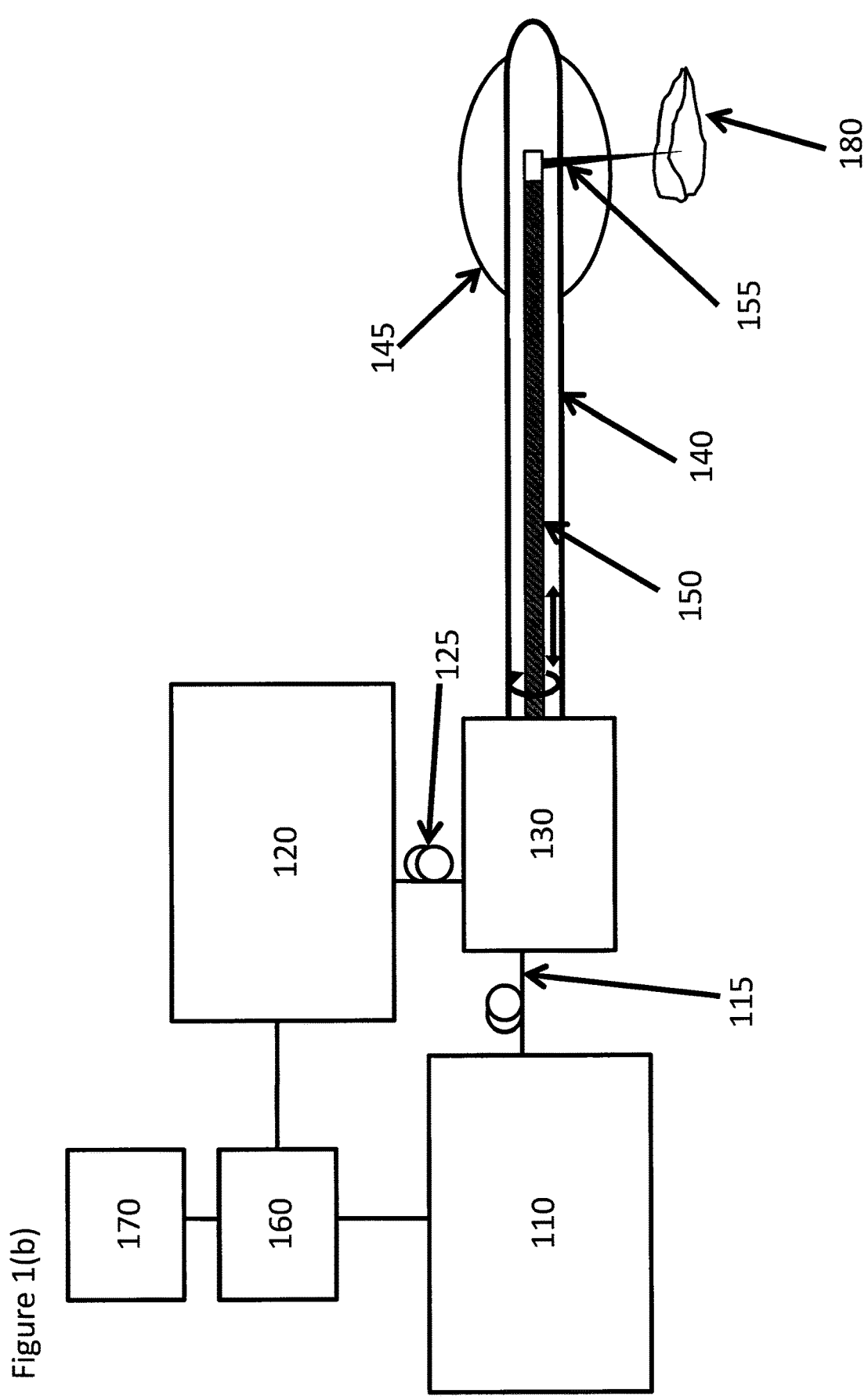
FIG. 1(b) is a schematic block diagram of the multi modality optical imaging catheter system and/or arrangement with a centering balloon for large luminal organs according to another exemplary embodiment of the present disclosure.

The dual modality rotary junction 130 can combine two different optical beams, and serve as the interface between the stationary imaging systems to the rotating and translating imaging catheter 150. The transparent imaging sheath 140 can be used to protect the imaging catheter 150 and the tissue 180, while the imaging catheter 150 rotates and translates and performs a helical scanning of the tissue. The optical imaging beam 155 can be focused by the dual-modality optical imaging catheter 150 onto the tissue 180. Returning light signals from the tissue 180 are detected by the microstructural imaging system 110 and the molecular imaging system 120. Both systems 110, 120 can be synchronized, and the signals can be acquired simultaneously by the data acquisition system 160. The data processing and storage arrangement/apparatus 170 can save and process the data in a real-time for the proper operation, and for subsequent visualization and analysis. As shown in FIG. 1(b), according to another exemplary embodiment of the present disclosure, a centering balloon 145 can be, e.g., provided and/or manufactured on the transparent imaging sheath 140 for imaging large luminal organs, such as esophagus, colon, etc.

For example, the molecular imaging system 120 can include facilitate the implementation of fluorescence imaging, multi-photon imaging, near infra-red fluorescence imaging, fluorescence spectroscopy, fluorescence lifetime imaging, Raman spectroscopy, near infra-red reflectance spectroscopy, etc. In fluorescence imaging, fluorescent contrast agents can be used to target specific molecules, cells, proteins, or enzymes, associated with diseases. By using the targeted contrast agents, specific information can be obtained with high contrast. In addition, endogenous auto-fluorescence can be obtained with the catheter system. Since auto-fluorescence imaging techniques do not need any administration of exogenous contrast agents, such exemplary technique can be used in diagnostic applications, as well as in research, without a significant concern of the toxicity. Typically, UV/Visible illumination is used for imaging collagen, elastin, NADH, and etc.

However, near infra-red light can be used in order to detect auto-fluorescence signal from lesions. Further, multi-photon imaging can be used as a molecular imaging modality using a pulsed laser with and without the exogenous contrast agents. Near infra-red fluorescence imaging procedures can illuminate and/or detect fluorescent emission(s) from the fluorochromes in the near infra-red region. Since the auto-fluorescence of the tissue is reduced and/or minimized in near infra-red region, exogenous fluorescent contrast agents can be imaged with high contrast with minimized back-ground noise. Due to the high contrast, a lower dose of the contrast agent can be used for the detection. In addition, fluorescence lifetime imaging can be used. By measuring the difference of the lifetimes of the fluorochromes, molecular composition of lesions can be identified.

Raman spectroscopy is another procedure that can be used to provide the chemical composition of biological tissues without exogenous contrast agents. By measuring the frequency shift of Raman scattering, chemical composition of the tissue, such as elastin, collagen, cholesterol, cholesterol esters, triglycerides, phospholipids, and calcium salts can be measured with a high accuracy. Near infra-red spectroscopy is another technique for identifying tissue components. For example, due to the different absorption and scattering property, different tissue types can be identified and quantified by measuring and analyzing optical spectrums of the reflected signal from the tissue.

FIG. 2(a) shows a schematic diagram of a multi modality optical imaging catheter with a side-viewing ball lens according to an exemplary embodiment of the present disclosure. The double-clad fiber 200 can be used for multi-modality imaging. The microstructural imaging modality can work with a single-mode fiber to facilitate the coherent interference between the light from the sample and one from the reference (not shown). Thus, a single-mode core 210 can be used to guide a single-mode light of the microstructural imaging modality.

For example, the molecular imaging modality can operate with a multi-mode fiber to facilitate the high collection efficiency for better signal-to-noise ratio. Since a multimode fiber have a larger diameter and a larger accepting angle than a single-mode fiber, the light efficiency is usually high. Thus, a multi-mode second clad 220 can be used to guide the multi-mode light of the molecular imaging modality. A ultra low index coating 230 can facilitate the multi-mode second clad 220 to function or operate as a multi-mode light guiding channel. A glass spacer 250 and a side-viewing ball lens 260 can be provided in a configuration and/or shape to focus the beams onto the tissue 180 with a proper resolution, focal length, confocal parameter, etc. according to the size and the properties of luminal organs. The light from the fiber expands while traveling through the glass spacer 250, then reflected by the polished surface, and focused by a curvature surface of the side-viewing ball lens 260.

Figure 2C:
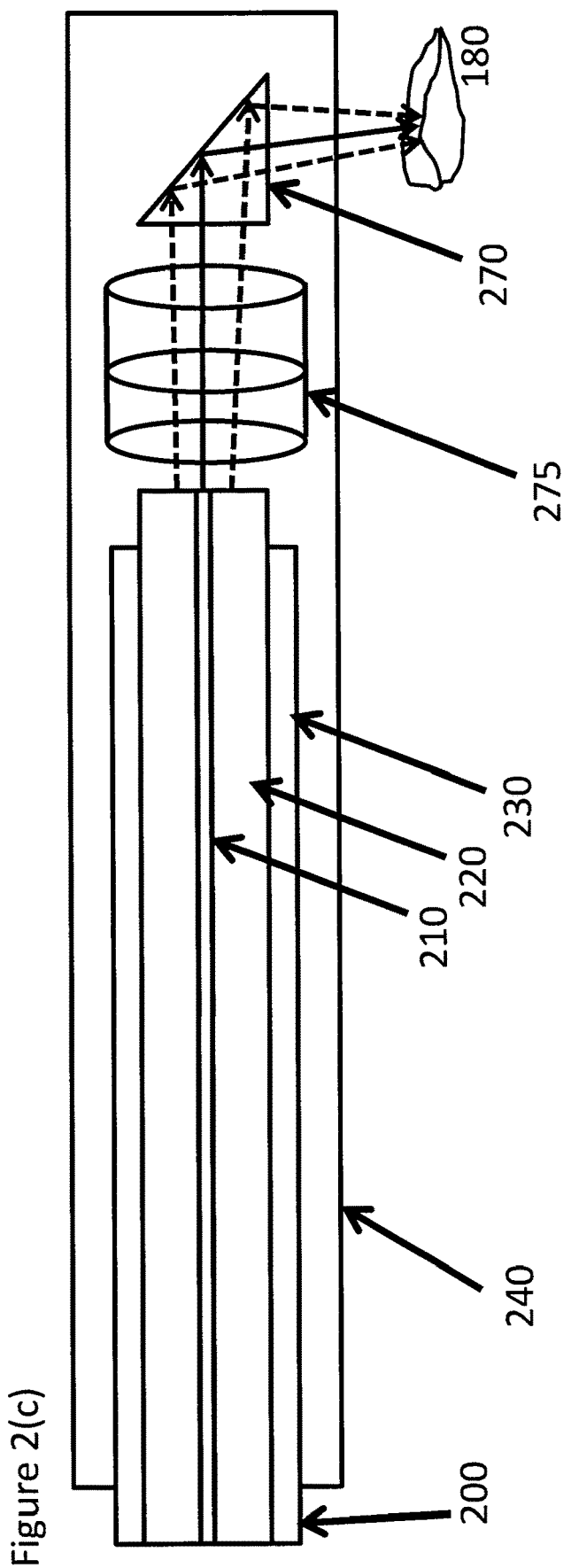
FIG. 2(c) is a side cross-sectional view of the multimodality optical imaging catheter with a micro-lens assembly and a prism according to still another exemplary embodiment of the present disclosure.

The curvature surface of the side-viewing ball lens 260 can be designed to eliminate the aberration induced by the transparent imaging sheath 140 and the centering balloon 145. Since the optical fiber 200, the glass spacer 250, and the side-viewing ball lens 260 can be manufactured in one body, the imaging catheter can be reliable and durable. The imaging fiber can be contained within a protective metal coil 240. The metal coil 240 can also facilitate fast rotation and/or translation of the imaging catheter, by transmitting the torque from the rotary junction to the imaging probe. Micro optics, such as a glass spacer 255, the GRIN lens and a prism 270, can be used instead of the side-viewing ball lens 260, as shown in FIG. 2(b). In addition, it is possible to utilize a micro-lens assembly 275 instead of or in addition to the side-viewing ball lens 260 or the GRIN lens for possibly improved optical performances as shown in FIG. 2(c). Since the micro-lens assembly can have a large number of components, such exemplary assembly can provide an improved optical performance with less aberrations.

According to one exemplary embodiment of the present disclosure, the double-clad fiber can be important for the multi modal imaging catheter since such exemplary fiber can have independent multiple light guiding channels, e.g., optimized for each of the imaging modalities. For example, a concentric arrangement of the double-clad fiber facilitates a continuous rotation of the imaging catheter which can transmit multiple optical signals as well as precise co-registration between different imaging modalities.

The exemplary double-clad fiber with ultra low index coating can include a single-mode core 210, a multi-mode second clad 220, and an ultra low index coating 230, as shown in FIG. 3(a). The single-mode core 210 can be designed to be the same as or similar to the standard single-mode fiber, so that the multi modality catheter can be at least approximately, and preferably substantially matched well with the microstructural imaging system that can be provided with or from the standard single mode fiber. The multi-mode second clad 220 can be same as or similar to the standard multi-mode fiber, so that the multi modality catheter can be at least approximately, and preferably substantially matched well with the molecular imaging system that can be provided from or with the standard multi mode fiber.

The ultra low index coating 230 can facilitate the second clad 220 to work as a multi-mode fiber. In addition, such coating 230 can mechanically protect the imaging channels. The cross-talk between the channels can deteriorate imaging quality of one or more of the imaging modalities. Thus, reducing and/or minimizing the cross-talk is preferable. For a better separation of the imaging channels, a cross-talk barrier 215 can be provided. For example, this can be facilitated by applying a low-index trench between the single-mode core 210 and the multi-mode second clad 220, as shown in FIG. 3(b). Another exemplary embodiment of a configuration of the double-clad fiber with two claddings is shown in FIG. 3(c). Depending on the properties of the fiber materials, the first clad 250 and the protective coating 260 can be provided for improved optical performance and mechanical protection. Addition, in such exemplary arrangement, the cross-talk barrier 215 can be used to reduce and/or minimize the cross-talk between the channels, as shown in FIG. 3(d).

Figure 4A:
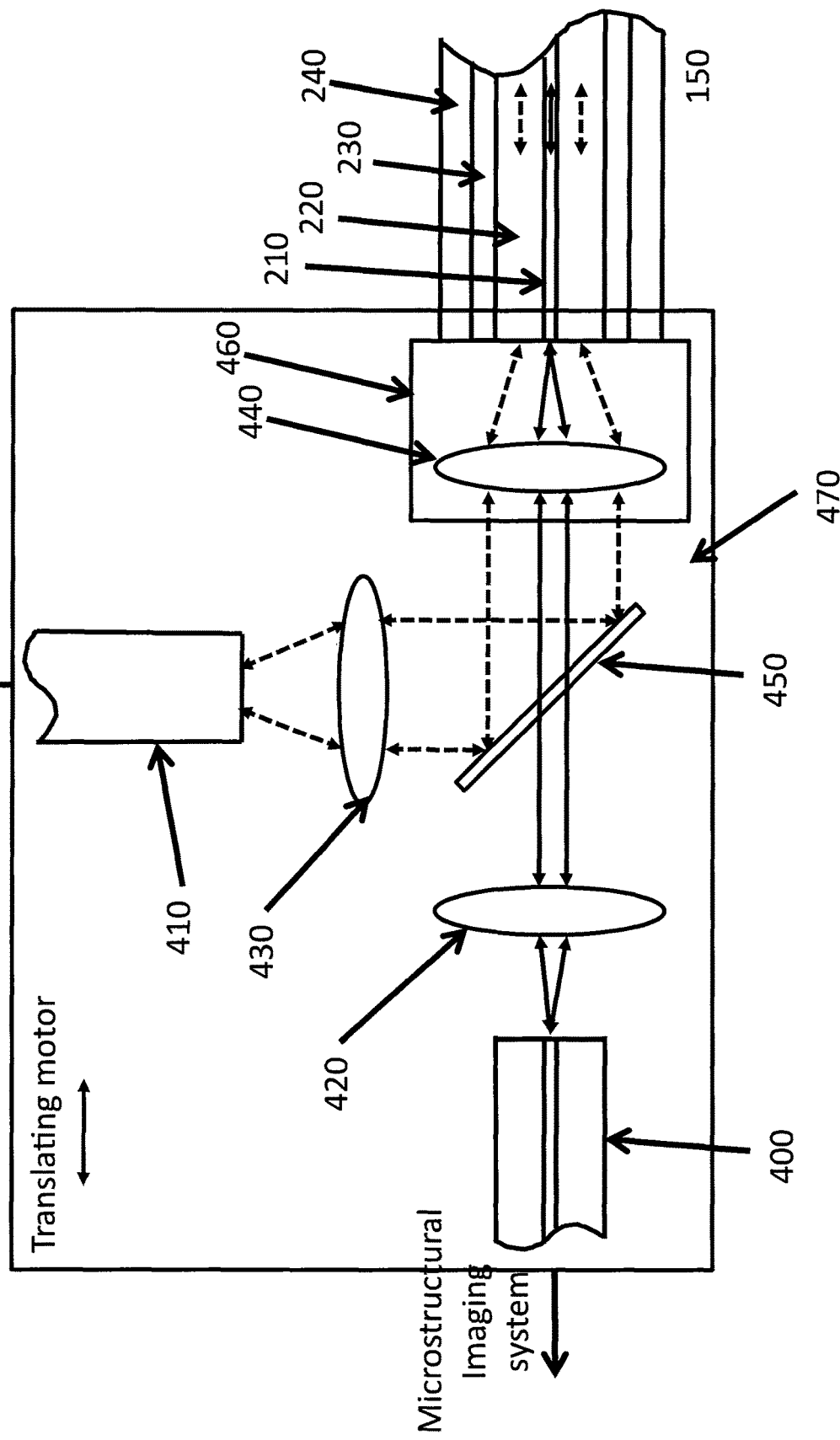
FIG. 4(a) is a schematic diagram of a system comprising a dual-modality rotary junction that uses a dichroic mirror for a rotating and translating catheter according to an exemplary embodiment of the present disclosure.
Figure 4B:
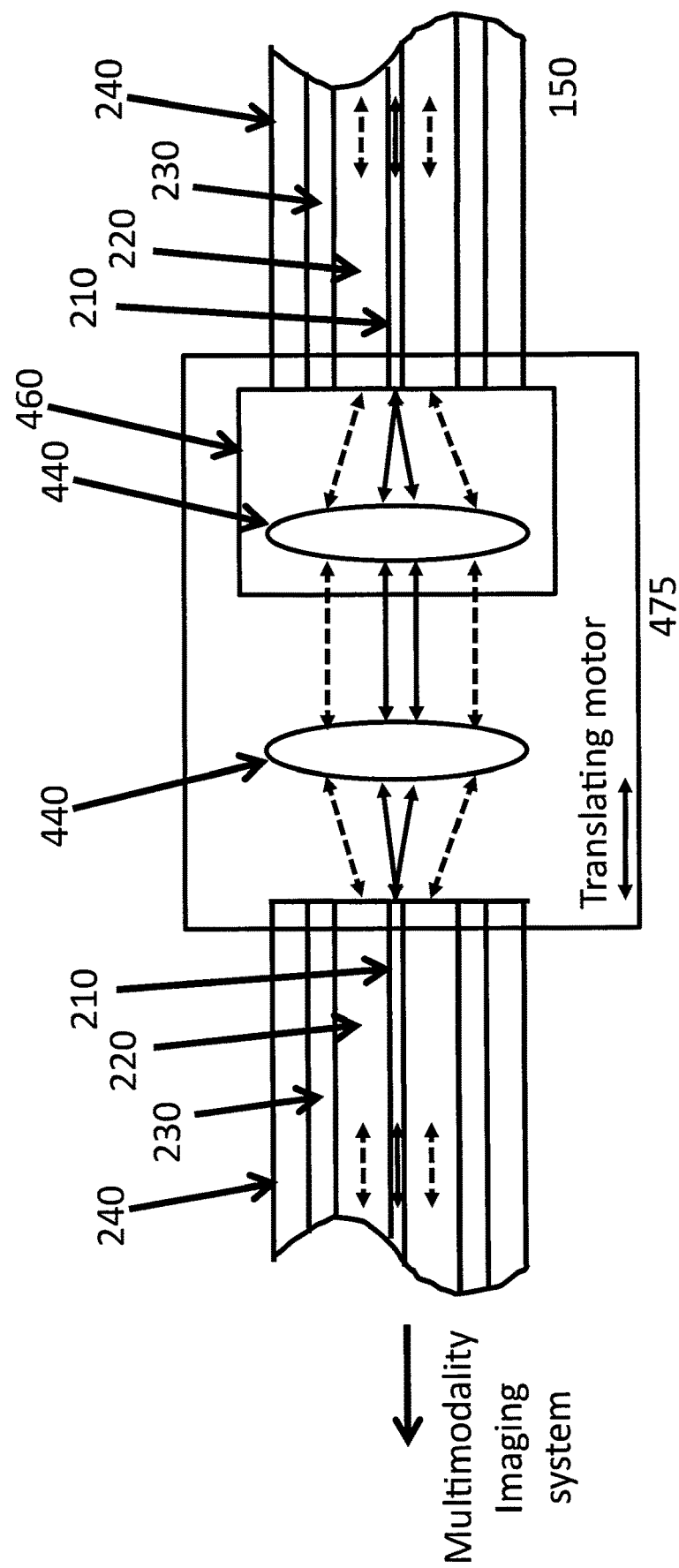
FIG. 4(b) is a schematic diagram of another system comprising the dual-modality rotary junction that uses a hole mirror for a rotating and translating catheter according to another exemplary embodiment of the present disclosure.

The dual-modality rotary junction 130 can be used for the rapid helical scanning that facilitates a comprehensive three-dimensional scanning of the luminal organs. A schematic diagram of an exemplary embodiment of dual-modality rotary-junction according to the present disclosure is shown in FIG. 4(a). This exemplary apparatus can include, e.g., a single mode fiber 400, a multi mode fiber 410, a collimating lens for microstructural imaging modality 420, a collimating lens for molecular imaging modality 430, an achromatic collimating lens for both microstructural and molecular imaging modality 440, a dichroic mirror, a beam splitter, or a hole-mirror 450, a rotary motor 460, and a translation motor 470.

In this exemplary embodiment, the single mode fiber 400 can deliver the single-mode light from the microstructural imaging system 110. The multi mode fiber 410 can deliver the multi-mode light from the molecular imaging system 120. The collimating lens 420 can be designed and/or arranged such that the microstructural imaging beam can be collimated with minimized optical aberration. The other collimating lens 430 can be designed to facilitate a reduction and/or minimization of optical aberrations for the molecular imaging beam. One or more light sources can be provided with different wavelength bands so that two or more different beams can be combined and divided by the dichroic mirror 450 with a high light throughput. If the wavelength ranges of the two imaging modalities are overlapped, they can be combined and divided by the beam splitter 450.

The achromatic collimating lens 440 can be provided to reduce and/or minimize optical aberration over the large range of the wavelength, so that both the microstructural imaging beam and the molecular imaging beam can be efficiently coupled into the catheter 150. The rotary motor 460 can rotate the achromatic collimating lens 440 and the dual-modality optical imaging catheter 150 for the circumferential scanning. The rotating torque can be transmitted through the protective metal coil 240. The rotating motor 460 can located on or near the translating motor 470. The translating motor 470 can longitudinally move the optical imaging catheter 150. A rotation of the rotary motor 460 and a translation of the translating motor 470 can facilitate a three-dimensional (3D) scanning of the luminal organ in a helical pull-back fashion.

A schematic diagram of a dual-modality rotary junction according to another exemplary embodiment of the present disclosure is shown in FIG. 4(c). In this exemplary apparatus, the double-clad fiber from the multi-modality imaging system can be coupled into the double-clad fiber of the multi-modality imaging catheter's double-clad fiber by the achromatic collimating lens pair 440. The beam splitting and combining procedure can be achieved at the proximal end of the multimodality imaging system's double-clad fiber using a dichroic mirror, a beam splitter, or a hole-mirror.

Figure 5:
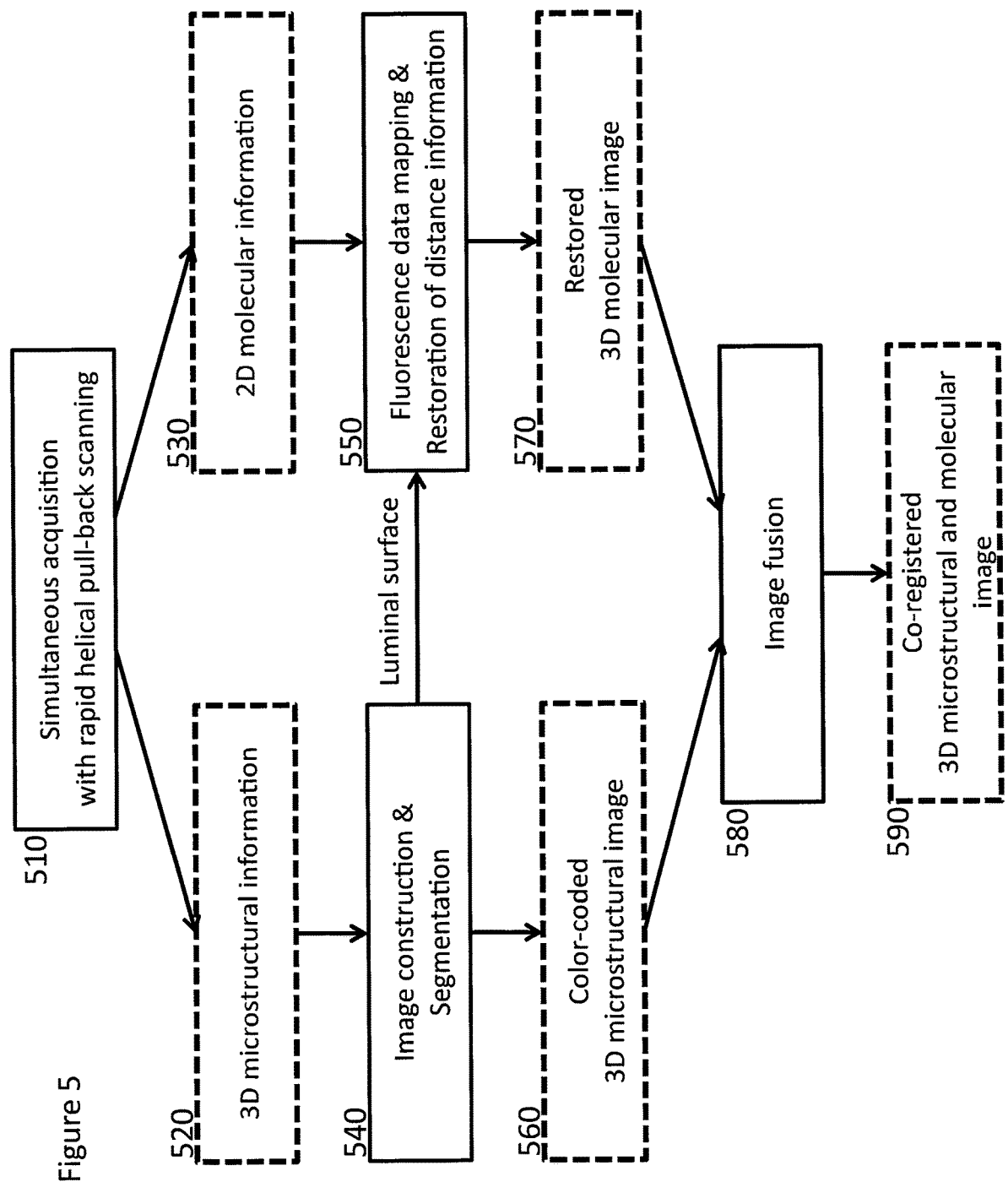
FIG. 5 is a flow diagram of an image fusion process for data obtained from the multi-modality catheter system and/or arrangement according to an exemplary embodiment of the present disclosure.

For example, multi-modality imaging data can be processed and fused for further visualization and analysis. FIG. 5 shows an image fusion process for data obtained from the multi-modality catheter system and/or arrangement according to an exemplary embodiment of the present disclosure.

As illustrated in FIG. 5, the simultaneous acquisition with rapid helical pull-back scanning, as provided in procedure 510, can be achieved by the exemplary multi-modality imaging system. For example, 3D microstructural information (procedure 520) can be obtained by OFDI and/or OCT procedures, and 2D molecular information (procedure 530) can be obtained by near infra-red fluorescence, fluorescence spectroscopy, Raman spectroscopy, and/or fluorescence lifetime imaging. Using image processing procedure 540, 3D microstructural information obtained in procedure 520 can be processed to form 3D images, then each biological components can be segmented according to their structural features. Thereafter the segmented images can be color-coded (procedure 560) for the 3D visualization.

In addition, quantitative information of each component can be extracted from the segmented images. While some molecular imaging modalities, such as confocal microscopy, diffuse optical tomography, photo-acoustic tomography, etc. can obtain depth information with a mechanical depth scanning or a post processing, many other molecular imaging modalities may not provide depth information, e.g., in a catheter form due to its space limitation. The distance information from the center to the luminal surface can be calculated in the segmented images. This information can be utilized to restore the distance information in the molecular information. Most of the molecular signal detected by the imaging catheter can be assumed to be provided from the luminal surface, by mapping the distance information (procedure 550) to the 2D molecular information. To that end, 3D molecular images obtained in procedure 570 can be restored. Then, using the image fusion procedure 580, co-registered 3D microstructural and molecular images can be calculated in procedure 590. These exemplary multi-modality images can be used for the qualitative and quantitative analysis of disease progresses of the luminal organs. Since the two imaging modalities can be obtained simultaneously and the imaging beams can be inherently co-registered due to the concentric double-clad fiber, two or more imaging modalities can be co-registered without spatial markers.

Figure 6:
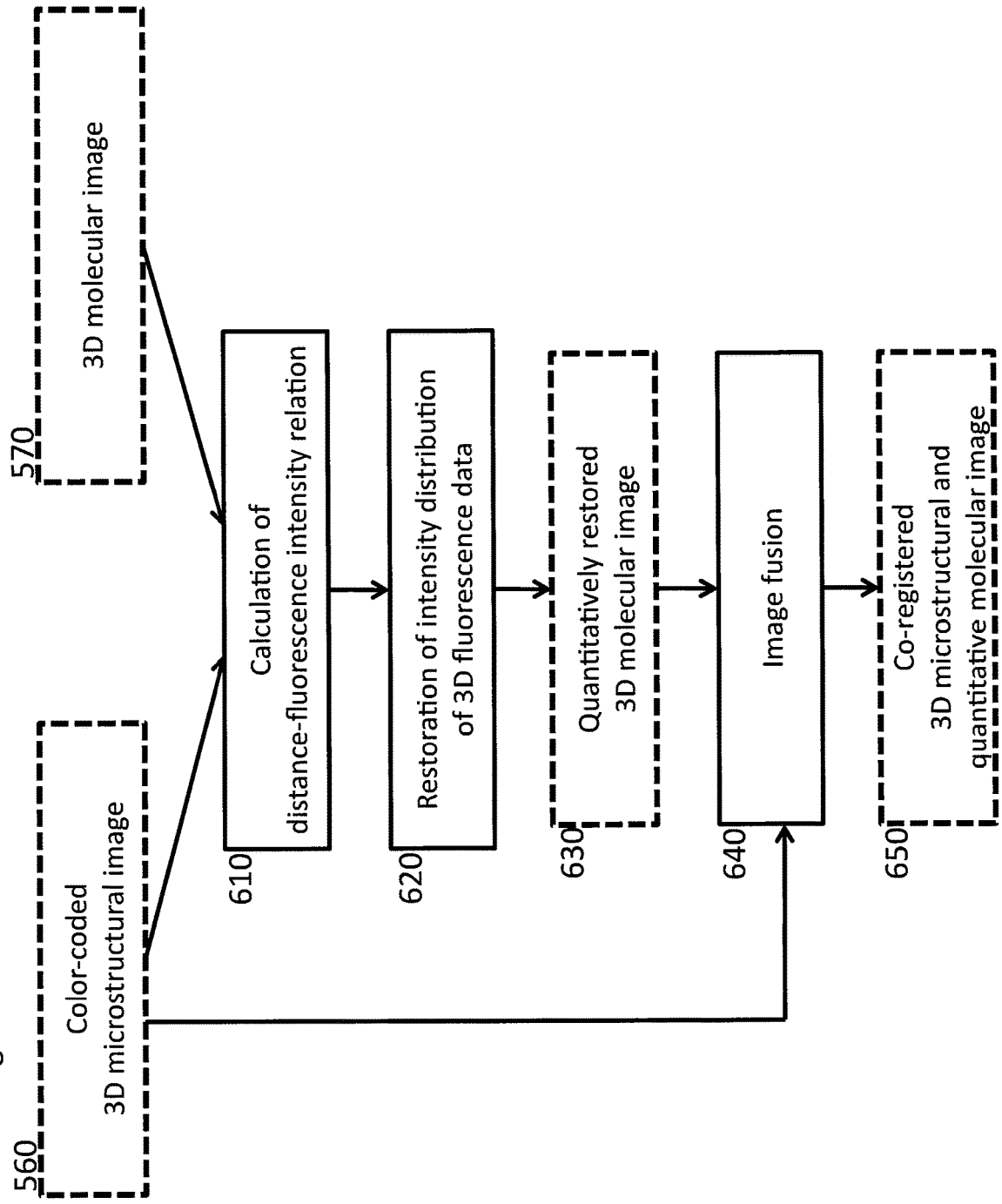
FIG. 6 is a flow diagram of an image reconstruction process for fluorescence data using OFDI data obtained from a multi-modality catheter system and/or arrangement according to an exemplary embodiment of the present disclosure.

Furthermore, because the microstructural imaging modality can provide the geometric information, molecular information can be restored for more accurate quantitative analysis. FIG. 6. shows an exemplary flow diagram of an image reconstruction process for fluorescence data using 3D microstructural images obtained from a multi-modality catheter system according to another exemplary embodiment of the present disclosure. Usually, in optical molecular imaging, the signal strength can depend on the distance. For example, the fluorescence signal strength is weaker when the distance from the imaging catheter to the tissue is farther. Thus the distance information can facilitate a restoration of the true signal strength. First, the relation between the distance and fluorescence intensity or energy can be (e.g., experimentally or theoretically) obtained in procedure 610. By inversely applying the relation to the fluorescence intensity according to the distance, the intensity distribution of 3D fluorescence data can be restored in procedure 620. This quantitatively restored 3D molecular image then can be fused (in procedure 630) with the 3D microstructural image for the further analysis by the image fusion algorithm obtained in procedure 640. In procedure 650, the co-registered 3D microstructural and quantitative molecular image can provide accurate quantitative information of the luminal organs.

FIGS. 7(a)-7(g) show exemplary experimental results on estimating concentration and distance compensation of the contrast agents for quantitative analysis provided by the exemplary systems, devices, methods, apparatus and computer-accessible media according to the present disclosure. For example, FIG. 7(a) shows a measured fluorescence signal while immersing the catheter in the solution repeatedly. FIGS. 7(b) and 7(c) show the measured fluorescence signal as a function of the concentration of the contrast agent, which showed a linear relationship. The fluorescence signal intensity was measured as a function of sample distance from the catheter in order to characterize the relationship between the NIRF intensity and the distance, as shown in FIG. 7(d). The measurements were fitted using an exponential function, then the calibration function for distance correction was generated, as shown in FIG. 7(e). After measuring the distance from the catheter to the luminal surface of the sample from the microstructural images, the fluorescence signal intensity was multiplied by the calibration function accordingly.

FIGS. 7(f) and 7(g) show the 2D fluorescence image of the capillary tube filled with the fluorescent contrast agent, before and after the distance calibration, respectively.

Figure 8D:
FIGS. 8(a)-8(d) are images providing experiment results due to an acquisition of multi-modality images of rabbit arteries in vivo with fluorescently labeled thrombus and a coronary stent by utilizing the exemplary systems, devices, methods, apparatus and computer-accessible media according to the present disclosure.
Figure 8C:
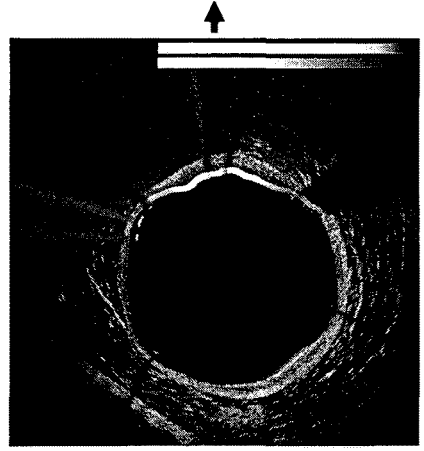
Figure 8B:
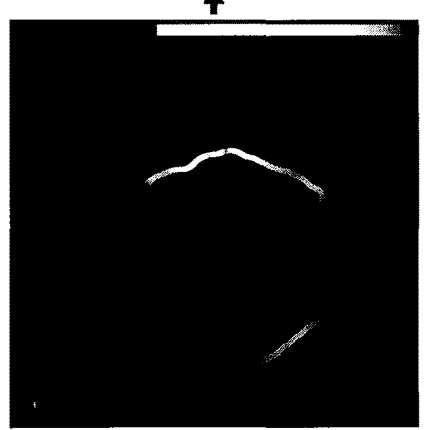
Figure 8A:
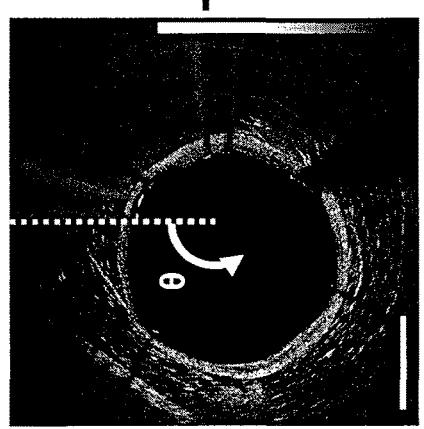

FIGS. 8(a)-8(d) are images providing experiment results due to an acquisition of multi-modality images of rabbit arteries in vivo with fluorescently labeled thrombus and a coronary stent provided by the exemplary systems, devices, methods, apparatus and computer-accessible media according to the present disclosure. In order to confirm the strength of acquiring the structural and molecular imaging simultaneously, a near infra-red (NIR) fluorescent fibrin-coated stent implanted into an excised cadaveric coronary artery was prepared. The coronary stent was rendered fluorescent in the NIR by incubating the stent with human fresh frozen plasma and a fibrin-targeted peptide derivatized with the NIR fluorochrome Cy7. For example, after implanting the fibrin-coated stent into the excised coronary artery, a guide-wire was introduced into the stented artery. Then the dual-modality catheter was advanced over the guide-wire so that the imaging range of the catheter was placed at the distal end of the artery. Simultaneous 3D OFDI and 2D fluorescence imaging of the sample were successfully acquired by the helical scanning pattern. FIG. 8(a) shows representative cross-sectional OFDI image and FIG. 8(b) shows the corresponding calibrated fluorescence signal mapped on top of the OFDI luminal surface. FIG. 8(c) shows the fused image of the microstructural OFDI image and the molecular NIRF image. Such 2D cross-sectional images were obtained by the helical scanning at different optical imaging catheter's positions with a specific interval. The 3D information then can be segmented and color-coded for the further 3D visualization as shown in FIG. 8(d). These imaging results show the feasibility of this technique and support the strength of multimodality imaging catheter for applications of the luminal organs, such as coronary artery imaging for accessing and interrogating coronary heart diseases.

The foregoing merely illustrates the principles of the invention. Various modifications and alterations to the described embodiments will be apparent to those skilled in the art in view of the teachings herein. Indeed, the arrangements, systems and methods according to the exemplary embodiments of the present disclosure can be used with and/or implement any OCT system, OFDI system, SD-OCT system or other imaging systems, and for example with those described in International Patent Application PCT/US2004/029148, filed Sep. 8, 2004 which published as International Patent Publication No. WO 2005/047813 on May 26, 2005, U.S. patent application Ser. No. 11/266,779, filed Nov. 2, 2005 which published as U.S. Patent Publication No. 2006/0093276 on May 4, 2006, and U.S. patent application Ser. No. 10/501,276, filed Jul. 9, 2004 which published as U.S. Patent Publication No. 2005/0018201 on Jan. 27, 2005, and U.S. Patent Publication No. 2002/0122246, published on May 9, 2002, the disclosures of which are incorporated by reference herein in their entireties. It will thus be appreciated that those skilled in the art will be able to devise numerous systems, arrangements and methods which, although not explicitly shown or described herein, embody the principles of the invention and are thus within the spirit and scope of the present disclosure. Further, the exemplary embodiments described herein can operate together with one another and interchangeably therewith. In addition, to the extent that the prior art knowledge has not been explicitly incorporated by reference herein above, it is explicitly being incorporated herein in its entirety. All publications referenced herein above are incorporated herein by reference in their entireties.

What is claimed is:

1. A method, comprising:
   providing a probe including an imaging system coupled to the probe and controlled by a computer arrangement, the probe comprising at least one optical fiber, the imaging system comprising at least one electro-magnetic radiation source coupled to the at least one optical fiber, and the computer arrangement comprising a processor;
   receiving, by the computer arrangement and from the imaging system, first data associated with at least one structure;
   determining, by the computer arrangement, a distance between the probe and the at least one structure based on the first data;
   receiving, by the computer arrangement and from the imaging system, second data associated with the at least one structure which is different from the first data, wherein the first and second data are obtained from substantially the same location on or in the at least one structure, and wherein the first data include structural information; and
   correcting, by the computer arrangement, a signal intensity associated with the second data based on the distance between the probe and the at least one structure to produce corrected second data, the corrected second data relating to at least one characteristic of the at least one structure.

2. The method according to claim 1, further comprising:
   ascertaining further information associated with the at least one structure based on the corrected second data; and
   determining the at least one characteristic of the at least one structure based on the further information.

3. The method according to claim 1, further comprising:
   generating a three-dimensional image of the at least one structure based on the first data;
   generating a two-dimensional image of a surface of the at least one structure based on the corrected second data; and
   co-registering the two-dimensional image with the three-dimensional image of the at least one structure to generate a multi-modality three-dimensional image.

4. The method according to claim 3, wherein co-registering the two-dimensional image with the three-dimensional image of the at least one structure further comprises:
   identifying the surface of the at least one structure in the three-dimensional image of the at least one structure based on segmenting the three-dimensional image of the at least one structure, and
   co-registering the two-dimensional image of the surface of the at least one structure with the three-dimensional image of the at least one structure to generate the multi-modality three-dimensional image.

5. The method according to claim 1, wherein the at least one electro-magnetic radiation source comprises a near-infrared radiation source, and
   wherein the second data are obtained using near-infrared spectroscopy (NIRS).

6. The method according to claim 1, wherein the at least one electro-magnetic radiation source comprises a visible light source, and
   wherein the second data are obtained using the visible light source.

7. The method according to claim 1, wherein the imaging system comprises an optical coherence tomography system and wherein the first data include optical coherence tomography data.

8. The method according to claim 1, wherein the imaging system comprises a fluorescence imaging system and wherein the second data include optical fluorescence data.

9. The method according to claim 1, wherein the distance is a distance from the probe to an artery wall of the at least one structure.

10. The method according to claim 1, wherein the distance is a distance from the probe to a tissue of the at least one structure.

11. The method according to claim 1, wherein the distance is a distance from the probe to a lumen of the at least one structure.

12. The method according to claim 1, wherein the further information relates to a concentration of a molecule or a chemical.

13. The method of claim 1, wherein the first data and the second data are received simultaneously.

14. The method of claim 1, wherein correcting the signal intensity associated with the second data based on the distance between the probe and the at least one structure further comprises:
   determining a calibration function to calibrate signal intensity based on a distance from the probe;
   applying the calibration function to the corrected second data to obtain calibrated second data; and
   wherein ascertaining further information associated with the at least one structure based on the corrected second data further comprises:
   ascertaining further information associated with the at least one structure based on the distance.

15. The method of claim 1, wherein the distance comprises a distance from the probe to a luminal surface of the at least one structure.

16. A non-transitory computer-accessible medium which includes instructions thereon for performing a procedure, wherein, when the instructions are executed by a computer arrangement comprising a processor, the computer arrangement is configured to perform procedures comprising:
   receive first data associated with at least one structure from an imaging system coupled to a probe, the probe comprising at least one optical fiber, and the imaging system comprising at least one electro-magnetic radiation source coupled to the at least one optical fiber;
   determine a distance between the probe and the at least one structure based on the first data;

receive second data associated with the at least one structure from the imaging system,
the second data being different from the first data,
the first and second data being obtained from substantially the same location on or in the at least one structure, and
the first data including structural information;
correct a signal intensity associated with the second data based on the distance between the probe and the at least one structure to produce corrected second data; and
correcting the second data based on the physical parameter further comprising correcting a signal intensity associated with the second data based on the physical parameter,
the corrected second data relating to at least one characteristic of the at least one structure.

17. The non-transitory computer-accessible medium according to claim 16, wherein the computer arrangement is further configured to:
ascertain further information associated with the at least one structure based on the corrected second data; and
determine the at least one characteristic of the at least one structure based on the further information.

18. The non-transitory computer-accessible medium according to claim 16, wherein the computer arrangement is further configured to:
generate a three-dimensional image of the at least one structure based on the first data;
generate a two-dimensional image of a surface of the at least one structure based on the corrected second data; and
co-register the two-dimensional image with the three-dimensional image of the at least one structure to generate a multi-modality three-dimensional image.

19. The non-transitory computer-accessible medium according to claim 18, wherein the computer arrangement, when co-registering the two-dimensional image with the three-dimensional image of the at least one structure, is further configured to:
identify the surface of the at least one structure in the three-dimensional image of the at least one structure based on segmenting the three-dimensional image of the at least one structure, and
co-register the two-dimensional image of the surface of the at least one structure with the three-dimensional image of the at least one structure to generate the multi-modality three-dimensional image.

20. The non-transitory computer-accessible medium according to claim 16, wherein the at least one electromagnetic radiation source comprises a near-infrared radiation source, and wherein the second data are obtained using near-infrared spectroscopy (NIRS).

21. The non-transitory computer-accessible medium according to claim 16, wherein the at least one electromagnetic radiation source comprises a visible light source, and
wherein the second data are obtained using the visible light source.

22. The non-transitory computer-accessible medium according to claim 16, wherein the imaging system comprises an optical coherence tomography system and wherein the first data include optical coherence tomography data.

23. The non-transitory computer-accessible medium according to claim 16, wherein the imaging system comprises a fluorescence imaging system and wherein the second data include optical fluorescence data.

24. The non-transitory computer-accessible medium according to claim 16, wherein the distance is a distance from the probe to an artery wall of the at least one structure.

25. The non-transitory computer-accessible medium according to claim 16, wherein the distance is a distance from the probe to a tissue of the at least one structure.

26. The non-transitory computer-accessible medium according to claim 16, wherein the distance is a distance from the probe to a lumen of the at least one structure.

27. The non-transitory computer-accessible medium according to claim 16, wherein the further information relates to a concentration of a molecule or a chemical.

28. The non-transitory computer-accessible medium according to claim 16, wherein the first data and the second data are received simultaneously.

29. The non-transitory computer-accessible medium according to claim 16, wherein the computer arrangement, when correcting the signal intensity associated with the second data based on the distance between the probe and the at least one structure, is further configured to:
determine a calibration function to calibrate signal intensity based on a distance from the probe;
apply the calibration function to the corrected second data to obtain calibrated second data; and
wherein the computer arrangement, when ascertaining further information associated with the at least one structure based on the corrected second data, is further configured to:
ascertain further information associated with the at least one structure based on the distance.

30. The non-transitory computer-accessible medium according to claim 16, wherein the distance comprises a distance from the probe to a luminal surface of the at least one structure.

* * * * *